(12) United States Patent
Gaillard et al.

(10) Patent No.: US 8,199,786 B2
(45) Date of Patent: Jun. 12, 2012

(54) LASER DIODE STRUCTURE WITH REDUCED INTERFERENCE SIGNALS

(75) Inventors: Mathieu Gaillard, Lausanne (CH); Bert Willing, Blonay (CH); Stefan Manzeneder, Sachseln (CH)

(73) Assignee: Leister Technologies AG, Kägiswil (CH)

( * ) Notice: Subject to any disclaimer, the term of this patent is extended or adjusted under 35 U.S.C. 154(b) by 83 days.

(21) Appl. No.: 12/779,144

(22) Filed: May 13, 2010

(65) Prior Publication Data

US 2011/0216793 A1   Sep. 8, 2011

(30) Foreign Application Priority Data

Mar. 3, 2010 (EP) ..................................... 10002153

(51) Int. Cl.
  *H01S 3/04* (2006.01)
(52) U.S. Cl. ............................. 372/34; 372/36; 372/101
(58) Field of Classification Search .................... 372/34, 372/36, 101; 438/25, 122, 125; 257/706, 257/E33.057, E33.058, E33.075
See application file for complete search history.

(56) References Cited

U.S. PATENT DOCUMENTS

| | | | | |
|---|---|---|---|---|
| 5,828,687 A * | 10/1998 | Colgan | ............................ | 372/92 |
| 6,002,702 A * | 12/1999 | Haeusler et al. | ............ | 372/50.12 |
| 7,394,841 B1 * | 7/2008 | Konttinen et al. | ........ | 372/45.013 |
| 2005/0068996 A1 * | 3/2005 | Narayan | .......................... | 372/20 |
| 2006/0251425 A1 | 11/2006 | Kupershmidt et al. | | |
| 2009/0059116 A1 * | 3/2009 | Furuya et al. | ................... | 349/61 |
| 2010/0002235 A1 * | 1/2010 | Willing et al. | ................. | 356/437 |
| 2011/0110390 A1 * | 5/2011 | Willing et al. | ............. | 372/45.01 |

FOREIGN PATENT DOCUMENTS

| | | |
|---|---|---|
| EP | 0 800 167 A2 | 10/1997 |
| JP | 60-185231 A | 9/1985 |
| JP | 8-043692 A | 2/1996 |
| JP | 2009-260118 A | 11/2009 |

OTHER PUBLICATIONS

Gerginov et al., "Diode lasers for fast-beam laser experiments", Optics Communications, North-Holland Publishing Co., Amsterdam, NL Jan. 1, 2001, pp. 219-230, XP004228384. (Submitting article—previously listed on IDS submitted on Jul. 29, 2010).
European Search Report for corresponding European Application No. EP 10 00 2153 dated Jun. 24, 2010.
Gerginov et al., "Diode lasers for fast-beam laser experiments", Optics Communications, North-Holland Publishing Co., Amsterdam, NL Jan. 1, 2001, pp. 219-230, XP004228384.

\* cited by examiner

*Primary Examiner* — Jessica Stultz
*Assistant Examiner* — Delma R Forde
(74) *Attorney, Agent, or Firm* — Renner, Otto, Boisselle & Sklar, LLP

(57) ABSTRACT

A laser diode structure for generating a collimated or divergent laser beam, preferably for application in gas detection, with a laser diode arranged in a closed housing, with the housing comprising a housing bottom, an exit window, electrical connections, a temperature control device for the laser diode, and an optical element for influencing the laser beam. The temperature control device carrying the laser diode is arranged on the housing bottom and the optical element is positioned at a distance from the laser diode. The invention proposes an electrically controllable power device for the cyclic alteration of the position and/or alignment of the optical element in relation to the laser diode so that the optical path length for the laser beam in the housing changes periodically. The oscillating motion of the optical element has the effect of time-averaging the etalon and/or self-mixing effects caused by the back-reflections of the laser beam in the housing, thereby reducing the optical noise of the laser diode structure.

13 Claims, 3 Drawing Sheets

LASER DIODE STRUCTURE WITH REDUCED INTERFERENCE SIGNALS

CROSS-REFERENCE TO RELATED APPLICATION

The present application claims priority under 35 USC §119 to European Patent Application No. 10 002 153.4 filed Mar. 3, 2010, the entire disclosure of which is incorporated herein by reference.

TECHNICAL FIELD OF THE INVENTION

The invention concerns a laser diode structure for generating a laser beam, preferably for application in gas detection. The laser diode structure has a laser diode arranged in a closed housing wherein the housing comprises a housing bottom, an exit window for the laser beam, electrical connections, a temperature control device for the laser diode, and an optical element for guiding and/or shaping the laser beam, with the optical element positioned at a distance from the laser diode. The temperature control device is arranged on the housing bottom and carries the laser diode.

Such a laser diode structure can be used, for example as a narrow-band radiation source in conjunction with a corresponding radiation detector, in order to determine the concentration of a certain gas in a mixture with other gases. With such gas sensors, the detection of the gas to be detected is usually achieved by making use of absorption spectroscopy. With this technology, a laser beam that is generated by the laser diode structure and tuned in its wavelength to the gas to be detected is directed through the gas mixture. The wavelength of the laser light is selected so that the laser light is strongly absorbed by the gas. The degree of absorption of the laser beam is then used as an indicator for the concentration of the gas to be detected.

DESCRIPTION OF THE RELATED ART

It is known that a mono-mode laser diode, for example a DFB or VCSEL laser diode where the tunability of the diode in terms of its emission wavelength by means of the operating temperature is exploited, can be used for scanning parts of the spectra of gases to be analyzed, and, in doing so, for detecting the gases on the basis of their characteristic spectral lines. The operating temperature of the laser diode is usually selected and kept constant by means of a thermo-electric temperature control device, for example a cooling Peltier element, and the tuning of the laser radiation emitted by the laser diode is achieved by a variation of the operating current of the laser diode. When using the laser diode structure in gas sensor technology, a high detection sensitivity, as needed for example in tunable diode laser spectroscopy (TDLS), requires that the laser radiation generated by the laser diode structure exit from the laser diode with minimal interference phenomena. Even very small back-reflections of the laser light of the laser beam emanating from the laser diode on reflecting surfaces of the housing, of a collimator lens, or of the exit window of the laser diode structure have the effect of self-mixing of the laser beam and/or etalons. Both effects cause optical noise that reduces the signal resolution in high-resolution testing devices and with weak gas absorptions.

SUMMARY OF THE INVENTION

The invention addresses the problem of significantly reducing or completely eliminating the etalons and/or the self-mixing of a laser diode due to back-reflections inside the housing of the laser diode structure in order to improve the resolution of the test signal.

According to the invention, this problem is solved by a laser diode structure with the characteristics as claimed. Advantageous embodiments are given in the related claims.

The invention is based on the core idea of time-averaging specifically the back-reflections of laser light into the laser aperture of the laser diode on reflecting surfaces of optical components in the housing and of housing walls of the laser diode structure. This can be achieved by slightly varying, continuously and cyclically, the optical path length for the laser beam between the reflecting surfaces and the laser aperture by means of a movable optical element. In this context, 'slight variation' means a change of the path length in a magnitude of the wavelength of the laser light. Beside the movable optical element, non-movable beam-shaping or beam-guiding optical elements may also be arranged in the beam path.

For the purpose of time-averaging portions of the laser beam generated by the laser diode that are reflected back to the laser aperture, the laser diode structure according to the invention comprises an electrically controllable power device for the cyclical change of the position and/or the alignment of the optical element relative to the laser diode. The movement of the optical element is coupled with a change of the optical path length between the laser diode and the movable optical element. The laser diode structure is capable of emitting collimated or divergent radiation. If the laser diode structure collimates the laser beam, it is possible to move the collimator lens itself or another optical element that is arranged between the collimator lens and whose position and/or alignment relative to the housing can be changed. With a collimator lens that is immovably connected with the housing, forming—for example—the exit window of the laser diode structure, the other optical element may consist of a deflecting mirror, for example. In the case where the laser diode structure is supposed to emit divergent radiation, i.e. where a collimator lens is not provided, the movable optical element may act in concert with a non-collimating exit window. The power device alters, with periodic oscillation, the optical path length for the laser beam in the housing of the laser diode structure. Preferably, the oscillation along the course of the laser beam up to the movable optical element is asynchronous with the modulation of the laser current of the laser diode with respect to the wavelength of the laser light.

Generally, there are three possibilities for changing the optical path length. The optical element may be moved either in the direction of the beam path, perpendicular to it, or may be rotated in the beam path. A combination of these types of motion is also possible. Regarding the first possibility, for example, it is possible to change the distance of the laser diode to a collimator lens by moving while oscillating the collimator lens along its optical axis. The alternative of moving, instead of the collimator lens, the laser diode that is supported by the temperature control device—usually a Peltier element—arranged on the bottom of the housing must be considered problematic. An actuator for moving the laser diode, for example in the form of a piezo component, arranged between the temperature control device and the laser diode or between the housing bottom and the temperature control device will always have a negative effect on the thermal stabilization of the laser diode. Even slight changes of the temperature of the laser diode have a negative effect on the wavelength stability and the quality of the laser beam. For the purpose of changing the optical path length, it would therefore not be favorable to move the laser diode cyclically inside the housing of the laser diode structure, specifically by continually altering its distance from the temperature control device and/or the housing bottom.

In preferred embodiments of the invention, the distance from the laser diode of the optical element, for example a collimator lens, a deflecting mirror, or some other optical element that affects the laser beam, can be influenced by means of the power device. In order to move the collimator lens, the deflecting mirror, and/or some other optical element altering the direction or the beam profile of the laser beam, the power device preferably comprises an electrical actuator that is connected to the movable optical element and to the housing, preferably the housing bottom. Here, a movable collimator lens consists of an optical element, preferably a microlens. In the case where the collimator lens forms the exit window, the deflecting mirror preferably consists of a micromirror. The microlens or the micromirror, respectively, may be arranged on a carrier connected with the actuator, or directly on the actuator itself. It proved to be expedient to use a carrier with a cantilever, with the carrier firmly attached to the actuator and the microlens or micromirror arranged on the cantilever extending laterally from the actuator.

Preferably, a translational motion, a swiveling motion, or a rotating motion of the optical element can be performed by means of the actuator. Depending on the operating direction of the actuator and its type of connection and its direction of connection with the optical element, this element can be moved cyclically as desired by the actuator in its position relative to the optical axis of the laser aperture of the laser diode. While retaining its angle of inclination relative to the laser beam emanating from the laser aperture, the optical element may be shifted for example only along or perpendicular to the optical path of the laser diode structure, or may be inclined around one or several spatial axes. The power device is also capable of handling a combination of one or several inclination directions with one or several translational directions.

Preferably, a microactuator in the form of a piezo oscillating element, an electro-mechanical drive system, or an electrostatic or a thermal control device is used as actuator. In all possible embodiments of the laser diode structure according to the invention, the power device also comprises a control system for applying a direct voltage and/or an alternating voltage portion to the actuator. In a favorite embodiment, the direct voltage portion of the actuator control system is used to align the laser beam with the radiation detector. Here, the control system is able to vary the amplitude, the frequency, and/or the wave shape of the alternating voltage portion for optimal time-averaging of the back-reflected laser light. For example, for the time-averaging of the back-reflections of laser light by means of a movable collimator lens, a microlens made of silicon may be provided that is attached to the actuator in such a way that the laser aperture is located in the focal plane of the microlens. The collimating microlens is positioned in such a way that it is several hundred micrometers distant, in the direction of extension of the laser beam (z-direction), from the laser aperture of the laser diode, for example the laser aperture of a VCSEL. For the averaging, the actuator is operated with an alternating voltage by the control system of the power device so that the position of the collimator lens above the laser aperture oscillates in the z-direction. The frequency of the alternating voltage is selected high enough to ensure that every measuring point is averaged over a sufficient number of positions. With this process, the etalons and/or self-mixing effects caused by the boundary surface of the microlens are averaged efficiently.

In a simple embodiment, for example a piezo oscillating element that changes its structural height when an electrical voltage is applied, can be used as actuator. In addition, it is advantageous to arrange the laser aperture in the focal plane of the collimator lens, but not in the focal point of the lens itself. In practice, a lateral displacement of the optical axis of the collimator lens relative to the optical axis of the laser aperture of 30 to 50 µm proved to be optimal. In addition, it is advantageous to attach the actuator lens to the actuator in such a way that the focal plane of the collimator lens is not perpendicular to the beam direction of the laser beam but is inclined at an angle of 10 to 30° relative to the laser beam.

In principle, instead of the collimator lens, any other beam-shaping elements that have the same effect may be used in the laser diode structure according to the invention. Such beam-shaping elements may consist, for example, of collimating microlenses made of many types of material, collimating mirrors, or collimating GRIN lenses. As collimating mirrors, convex mirrors, parabolic mirrors, off-axis parabolic mirrors, or elliptical mirrors etc. may be used for example. As movable optical element or as fixed optical element, it is also possible to use diffractive optical components.

For the purpose of time-averaging the back-reflections of laser light towards the laser aperture of the laser diode it is also possible to continuously swivel back and forth the axis of the laser beam relative to the axis of the collimator lens. This results in continuously different path lengths for the back-reflections, which has the effect of effectively averaging the related interference effects. In order to continuously swivel the beam axis of the laser beam in an oscillating manner, it is possible, for example, to attach the movable deflecting mirror to the actuator in such a way that the laser beam first hits the mirror surface before reaching the surface of the collimator lens. In order to keep the structural size of the laser diode structure small, it is possible, for example, to use a so-called micromirror with a mirror surface size of only a few square millimeters.

The deflecting mirror can be rotated around at least one axis. Typically, such a micromirror is operated with a direct voltage on which an alternating voltage is superimposed. By means of the direct voltage, the neutral position of the micromirror can be defined, while the alternating voltage serves to continuously swivel the micromirror back and forth around the neutral position. Since over an optical path length of the laser beam of approximately 1 to 2 mm it is necessary to generate path differences of approximately 1 to 2 µm for the effective time-averaging of the back-reflections, very small deflections of the deflecting mirror around the neutral position are sufficient for this. By rotating the axis of the laser beam, these path differences are continuously being generated for all possible reflecting surfaces so that an arrangement of this type allows efficient averaging across all occurring optical interferences. This largely suppresses interfering effects caused by etalons or self-mixing. The setting of the neutral position of the laser beam by means of the direct voltage portion that moves the micromirror can additionally be employed for the automatic adjustment of the laser beam towards a photo detector. Here, a micromirror that can be deflected around two axes by the actuator is an advantage. It appears that a deflecting mirror of this type is clearly superior to a mirror that can be deflected in a single axis only.

Preferably, in all possible embodiments of the laser diode structure according to the invention, the exit window, the collimator lens, and/or the deflecting mirror are arranged relative to the laser diode in such a way that their optical axes are tilted in relation to the optical axis of the laser aperture of the laser diode. Here, the angle of inclination is selected so that back-reflections occurring at the exit window, the collimator lens, or the deflecting mirror will miss the laser aperture.

The proposed laser diode structure is not limited to VCSELs but can be used analogously for DFBs and any other type of diode lasers. Specifically, such a laser diode structure may include the combination of a movable collimator lens with a movable deflecting mirror.

Below, the invention is explained in detail with reference to three embodiments shown in the drawing. Additional characteristics of the invention are given in the following description of the embodiments of the invention in conjunction with the claims and the figures of the attached drawing. The individual characteristics of the invention may be realized either individually by themselves or in combinations of several in different embodiments of the invention.

DETAILED DESCRIPTION OF THE INVENTION

Figure 1:
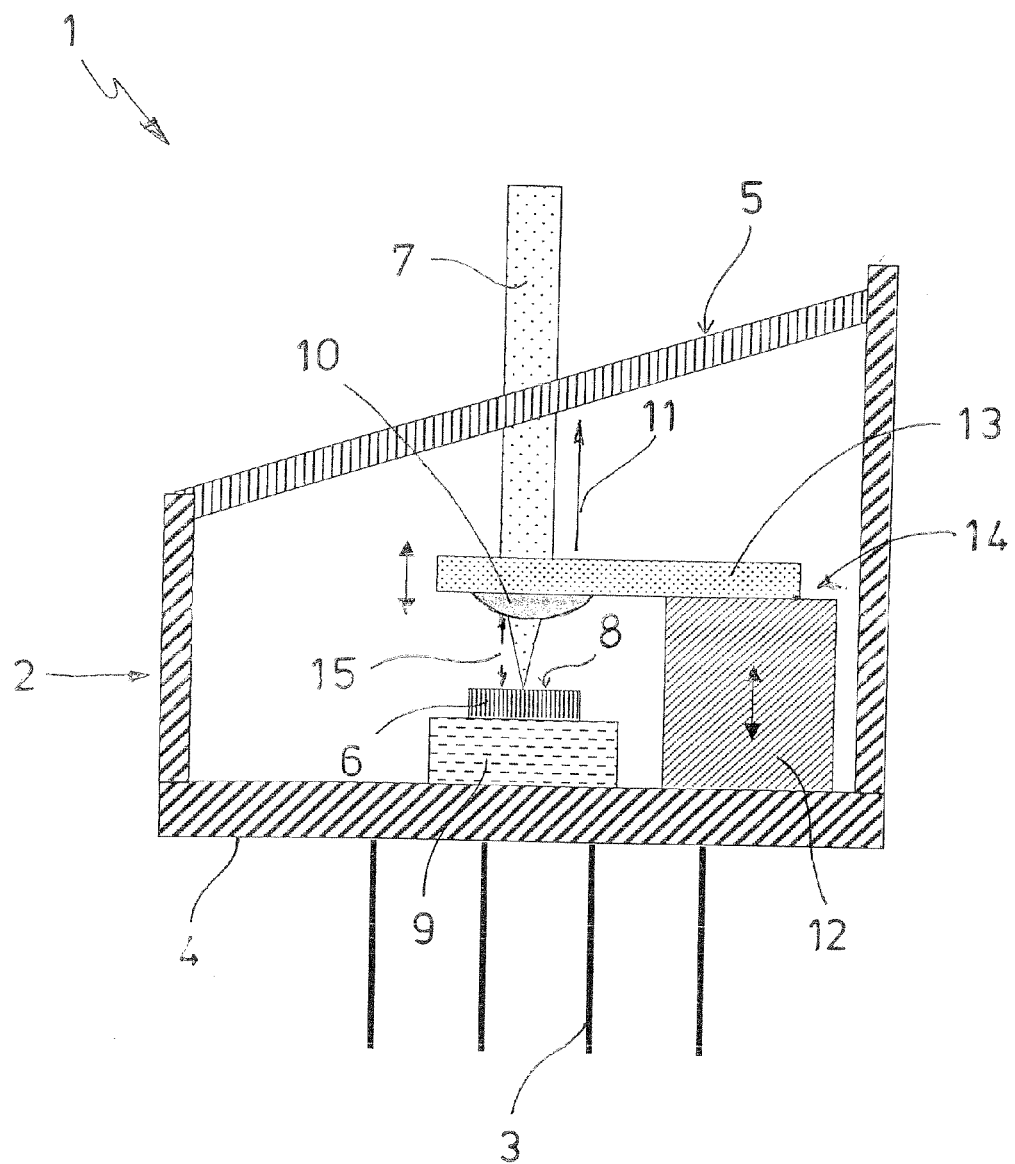
FIG. 1 shows a first laser diode structure according to the invention with a movable microlens arranged parallel to the laser aperture of the laser diode.

FIG. 1 shows a first embodiment of a laser diode structure 1 according to the invention, with a hermetically enclosed housing 2 that comprises a number of electrical connections 3 on a housing bottom 4 of the housing 2. Opposite the housing bottom 4, an exit window 5 is provided for the exit from the housing 2 of a laser beam 7 emitted by a laser diode 6. The exit window 5 extends at an angle to the housing bottom 4 of the housing 2 and to a laser aperture 8 of the laser diode 6. The laser diode 6 is mounted on a temperature control device 9 that is formed by a Peltier element. The Peltier element 9 is arranged on the housing bottom 4 and carries the laser diode 6 on a cold flat surface. With its warm flat surface on the opposite side, the Peltier element 9 is connected with the housing bottom 4 in a thermally well-conductive way. In addition, beside the laser diode 6, a thermistor (not shown) that serves as thermal sensor and controls the operating current of the Peltier element may be arranged on the Peltier element 9.

Between the laser diode 6 and the exit window 5 of the laser diode structure 1, and covering the laser aperture 8, a collimator lens 10 for collimating the laser beam 7 is arranged. The collimator lens 10 is arranged at a distance and parallel to the laser aperture 8 of the laser diode 6, and consists of a microlens. The distance from the laser aperture 8 is approximately 2 mm. By means of an actuator 12 in the form of a piezo oscillating element, the microlens 10 can be moved in and against the extension direction 11 of the laser beam 7 in dependence on the wavelength of the laser light by typically 1 to 3 μm. The piezo oscillating element 12 is arranged on the housing bottom 4 next to the Peltier element 9, with the collimator lens 10 being carried by a cantilever 13 extending laterally from the piezo oscillating element 12. Typically, the microlens 10 is displaced by approximately 30 to 50 μm in the transverse direction relative to the laser aperture 8 and therefore to the laser beam 7. This displacement, which cannot be seen clearly in the drawing, has the effect that possible back-reflections of the laser beam 7 from the microlens 10 occurring parallel to the emitted laser beam 7 will miss the laser aperture 8.

Together with the cantilever 13, the actuator 12 forms an electrically controllable power device 14 that is capable of continually and cyclically altering an optical path length 15 between the collimator lens 10 and the laser diode 6 by means of a control system (not shown). The position of the collimator lens 10 that continually changes over time may be determined by various types of deflection. For example, the control system may apply a sawtooth-shaped, sinoidal, stochastic, or Gauss-distribution-like control signal of random amplitude or random frequency to the actuator 12.

Also, in order to reliably prevent interfering back-reflections towards the laser aperture 8 of the laser diode 6 that originate at the exit window 5 of the housing 2, the exit window 5 is arranged on the housing 2 of the laser diode structure in an inclined configuration relative to the collimator lens 10 and the laser aperture 8. For this reason, portions of the laser beam 7 reflected by the exit window 5 will miss the collimator lens 10 and will not hit the laser aperture 8. This reliably prevents self-mixing.

Figure 2:
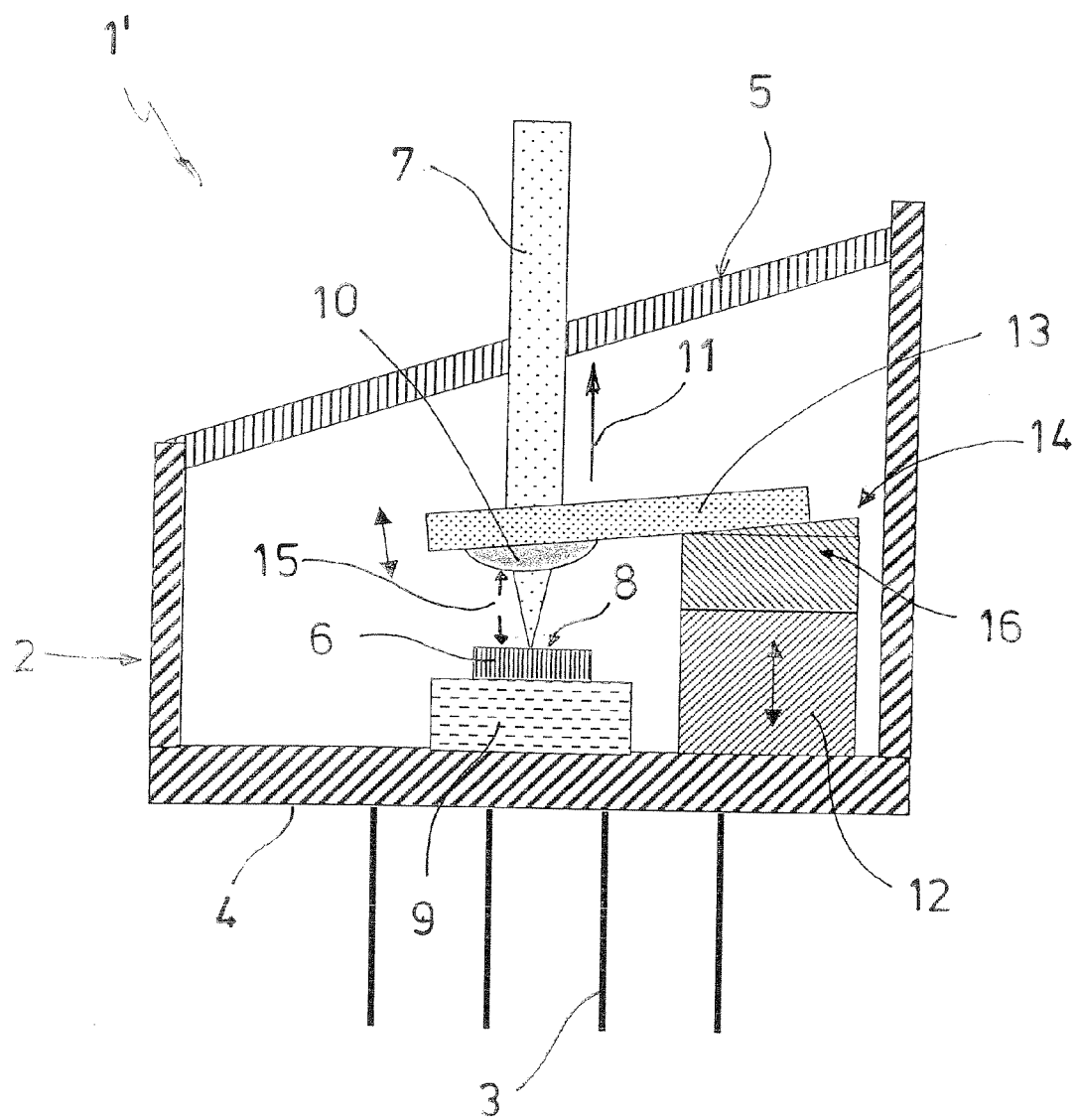
FIG. 2 shows a second laser diode structure according to the invention with a movable microlens arranged at an inclination relative to the laser aperture.

FIG. 2 shows a second embodiment of the invention that is similar to the first embodiment. The laser diode structure 1' according to the invention shown in FIG. 2 differs from the laser diode structure 1 shown in FIG. 1 only by the angled position of the collimator lens 10 relative to the laser beam 7. In the laser diode structure 1, the collimator lens 10 extends orthogonally to the laser beam 7, and in the laser diode structure 1' it extends at an angle that is different from 90° (tilt angle). Preferably, the tilt angle is between 10 and 30°. With the collimator lens 10 tilted relative to the extension direction 11 of the laser beam 7, portions of the laser beam 7 that are reflected by the collimator lens 10 are guided past the laser aperture 8 of the laser diode 6. Through this measure, self-mixing effects due to the reflection of the laser light on the boundary surfaces of the collimator lens 10 are significantly reduced, and the time-averaging of the other occurring etalons becomes considerably more efficient.

In order to tilt the cantilever 13 relative to the laser beam 7, a tilt wedge 16 is provided between the actuator 12 and the cantilever 13 which, together with the cantilever 13 and the actuator 12, forms the power device 14 in this case. The collimator lens 10 is arranged parallel to the cantilever 13 and thereby extends transversely to the laser beam 7. For a similar distance between the collimator lens 10 and the laser aperture 8, the actuator 12 is of lower-height design than in the laser diode structure 1 shown in FIG. 1. By means of the actuator 12, and with its tilt angle remaining the same in relation to the laser beam 7, the collimator lens 10 can be moved back and forth with an oscillating motion in relation to the laser diode 6.

Figure 3:
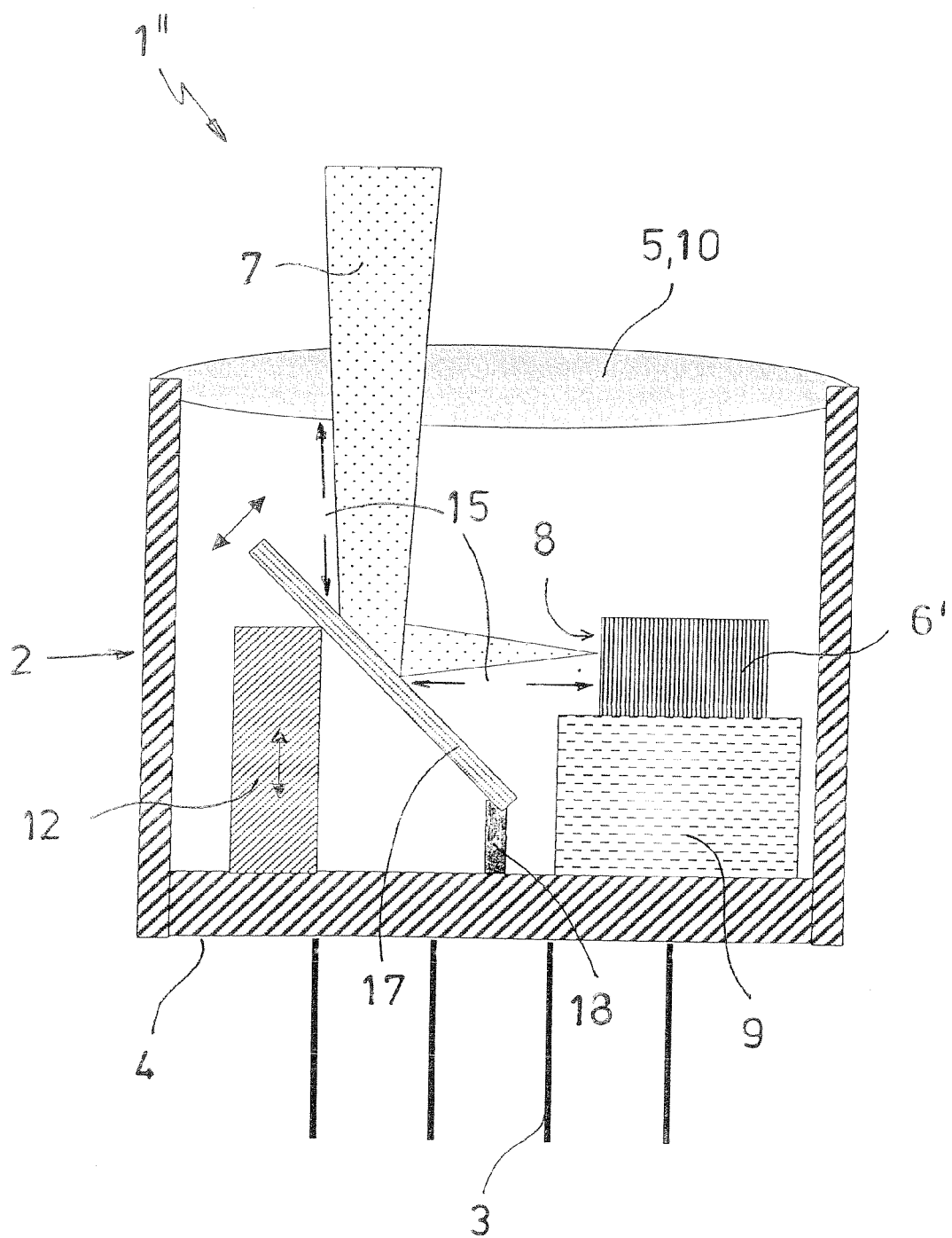
FIG. 3 shows a third laser diode structure according to the invention with a movable micromirror arranged at an inclination relative to the laser aperture of the laser diode.

FIG. 3 shows a third embodiment of the laser diode structure according to the invention. In the laser diode structure 1" shown here, the collimator lens 10 simultaneously forms the exit window 5 which in this case is arranged parallel to the housing bottom 4 of the housing 2. Like the laser diodes 6 in the laser diode structures 1, 1', the laser diode 6' is carried by a temperature control device 9 that is arranged eccentrically on the housing bottom 4. Compared with the laser diodes 6 used in the laser diode structures 1, 1', the laser diode 6' has a laser aperture 8 that is provided laterally on the laser diode 6'. After exiting from the laser aperture 8, the laser beam 7 is deflected by a deflecting mirror 17 in the form of a micromirror in the direction of the collimator lens 10.

On the one hand, the micromirror 17 is swivelably connected to a holder 18 that is attached to the housing bottom 4 next to the temperature control device 9, and, on the other hand, it is connected, at a distance from the holder 18, to the actuator 12 which is also arranged on the housing bottom 4. By means of the actuator 12, the inclination of the deflecting mirror 17 can be continually and cyclically swiveled relative to the laser aperture 8, and therefore relative to the laser beam 7, and also relative to the collimator lens 10 that forms the exit window 5. Together with the holder 18, the actuator 12 forms the electrically controllable power device 14 that makes it possible to continually and cyclically alter an optical path length 15 between the collimator lens 10 and the laser diode 6'. As in the two embodiments described above, the actuator 12 is controlled by a control system (not shown) of the power device 14 that controls the actuator 12 with an alternating voltage in a similar way as in the laser diode structures 1, 1'. The alternating voltage may be superimposed onto a direct voltage that can be used to define the neutral position of the micromirror 17. By swiveling the laser beam 7 relative to the collimator lens 10 by means of the micromirror 17, path differences of the laser beam 7 are generated for all possible reflecting surfaces in the housing 2 of the laser diode structure 1" so that an efficient averaging across all occurring optical interferences is achieved. This largely suppresses interfering effects due to etalons or self-mixing.

Further features of the invention can be found in the description of preferred embodiments of the invention in connection with the claims and the drawings. The single features can be realised alone or several together in embodiments of the invention.

The invention claimed is:

1. A laser diode structure for generating a laser beam, preferably for application in gas detection, with a laser diode arranged in a closed housing, with the housing comprising a housing bottom, an exit window for the laser beam, electrical connections, a Peltier element as an active temperature control device for the laser diode, and an optical element for guiding and/or shaping the laser beam, with the Peltier element being arranged on the housing bottom and carrying the laser diode, and with the optical element positioned at a distance from the laser diode, wherein the laser diode structure comprises an electrically controllable power device that cyclically alters the position of the optical element relative to the laser diode by moving the optical element in and contrary to the propagation direction of the laser beam, thereby varying the distance in the propagation direction of the laser beam between the laser diode and the optical element, wherein the distance changes with periodic oscillation in a magnitude of the wavelength of the laser beam and therewith the optical path length between the laser diode and the optical element in an equal manner, and where the power device is arranged beside the Peltier element on the housing bottom.

2. A laser diode structure according to claim 1, wherein the optical element is a lens for collimating the laser beam of the laser diode.

3. A laser diode structure according to claim 1, wherein the optical element is a diffractive optical element.

4. A laser diode structure according to claim 1, wherein the optical element is a deflecting mirror for guiding the laser beam of the laser diode.

5. A laser diode structure according to claim 1, wherein the power device has an electrical actuator that connects the optical element with the housing, preferably with the housing bottom.

6. A laser diode structure according to claim 5, wherein a translational motion, a swiveling motion, or a rotating motion of the optical element can be performed by means of the actuator.

7. A laser diode structure according to claim 1, wherein a direct voltage portion and/or an alternating voltage portion can be applied to the actuator by means of a control system of the power device.

8. A laser diode structure according to claim 7, wherein the control system varies the amplitude, the frequency, and/or the wave shape of the alternating voltage portion.

9. A laser diode structure according to claim 5, wherein the actuator is a microactuator, preferably a piezo oscillating element, an electro-mechanical drive system, an electrostatic or a thermal control device.

10. A laser diode structure according to claim 1, wherein the exit window, the collimator lens, and/or the deflecting mirror have optical axes that are tilted in relation to an optical axis of the laser aperture of the laser diode.

11. A laser diode structure according to claim 6, wherein the actuator is a microactuator, preferably a piezo oscillating element, an electro-mechanical drive system, an electrostatic or a thermal control device.

12. A laser diode structure according to claim 7, wherein the actuator is a microactuator, preferably a piezo oscillating element, an electro-mechanical drive system, an electrostatic or a thermal control device.

13. A laser diode structure according to claim 1, wherein the electrically controllable power device is configured to move the optical element in and contrary to the propagation direction of the laser beam by 1 μm to 3 μm.

* * * * *